US005889833A

United States Patent [19]
Silver

[11] Patent Number: 5,889,833
[45] Date of Patent: Mar. 30, 1999

[54] HIGH SPEED COMPUTED TOMOGRAPHY DEVICE AND METHOD

[75] Inventor: Michael D. Silver, Northbrook, Ill.

[73] Assignee: Kabushiki Kaisha Toshiba, Kawasaki, Japan

[21] Appl. No.: 877,211

[22] Filed: Jun. 17, 1997

[51] Int. Cl.$^6$ ........................................................ A61B 6/03
[52] U.S. Cl. ................................ 378/15; 378/19; 378/901
[58] Field of Search .................................... 378/4, 15, 19, 378/901

[56] References Cited

U.S. PATENT DOCUMENTS

| 5,355,309 | 10/1994 | Eberhard et al. | 378/15 |
| 5,430,784 | 7/1995 | Ribner et al. | 378/19 |
| 5,625,660 | 4/1997 | Tuy | 378/15 |

*Primary Examiner*—David P. Porta
*Assistant Examiner*—David Vernon Bruce
*Attorney, Agent, or Firm*—Oblon, Spivak, McClelland, Maier & Neustadt, P.C.

[57] ABSTRACT

An x-ray computed tomography device and method where backprojection is performed with pixels each having their own back projection range. The range is determined using a two-dimensional completeness condition such that every line through a reconstructed slice must intercept the projection of the source orbit onto the plane of the slice. The completeness condition provides an adequate amount of data for the back projection to maintain quality of the reconstructed image while allowing a higher helical pitch ratio. This is advantageous in situations where fast scanning is desired, such as patient screening and CT-angiography. The method and device are preferably applied to a helical cone beam system. The backprojection can be performed using cone-beam projection data obtained with a helical scan or after sorting the projection data into parallel-beam ray-sums in the transverse plane while maintaining the cone angle. The sorting advantageously further increases the helical pitch ratio and thus increases scanning speed and reduces scanning time. The two types of backprojection may each use either the full projection data set or a minimal data set determined based upon the completeness condition.

40 Claims, 15 Drawing Sheets

HIGH SPEED COMPUTED TOMOGRAPHY DEVICE AND METHOD

BACKGROUND OF THE INVENTION

1. Field of the Invention

The present invention relates to an x-ray computed tomography device and method, and more particularly to a high-speed, high helical pitch cone-beam x-ray computed tomography device and method.

2. Discussion of the Background

As shown in FIG. 1, an x-ray computed tomography (CT) device includes an x-ray tube 10 for irradiating a beam of x-rays, typically of cone shape, through a collimator 11, and a detector array 12 for detecting x-rays passed through an object, such as patient 13 (who typically lies on a patient bed 14). Detector 12 is positioned at a side opposite to the x-ray tube 10 with respect to the object and a tomographic image can be obtained by rotating the x-ray tube 10 integrally with the detector 12 around the object (shown by path 15) in order to scan the object and reconstruct the projected data. Typically, the tube 10 and detector 12 are circularly rotated using a gantry (not shown) while translating patient 13 to produce a helical path. A center of rotation 16 normally intersects with the approximate cross-sectional center of the object being scanned.

In helical scans the pitch is defined as the axial translation velocity of the patient table, v, multiplied by the rotation period, T. If w is the nominal slice width (the axial aperture of a single element of the x-ray detector projected at rotation center of the scanner) then the helical pitch ratio is given as $$r_H = vT/w,$$

the ratio of the helical translation per gantry revolution to the projected axial aperture of a detector element.

In some applications, such as patient screening and CT-angiography (CTA), throughput is more important than obtaining the best possible diagnostic image quality. In the case of CTA, shorter scan times improves imaging because of a reduction in patient motion artifacts. However, conventional CT scanners, which typically have one row of detectors, require many rotations to cover the patient volume of interest and generally keep $r_H \leq 2$. It is difficult to shorten the scan time while maintaining acceptable image quality.

Also, reconstruction is typically carried out using a back projection method with fixed integration limits. In other words, the reconstruction typically interpolates the closest beams to a reconstruction pixel.

SUMMARY OF THE INVENTION

An object of the present invention is to provide an x-ray computed tomography device and method having short scan times while maintaining diagnostic image quality.

Another object of the present invention is to provide an x-ray computed tomography device and method where the helical scanning operation satisfies a two-dimensional completeness condition.

A further object of the present invention is to helically scan an object such that each pixel in the object has at least a minimum data coverage for image reconstruction.

A still further object of the invention is to reconstruct an image in an x-ray computed tomographic device such that pixels are allowed to have their own backprojection range.

These and other objects are achieved by an x-ray computed tomography device having a backprojection circuit where pixels in image reconstruction have a backprojection range. Each pixel may have its own back projection range. The back projection range may be determined using a completeness condition. Backprojection and completeness condition circuits supply this information to the backprojection circuit. The completeness condition is preferably a two-dimensional "weak" completeness condition where every line through a reconstructed slice of an image must intercept the projection of a source orbit onto the plane of the slice. Using these conditions a larger helical pitch of the device can be achieved while maintaining image quality.

The invention is preferably applied to cone-beam geometry. A cone-beam is scanned to produced cone-beam projection data. The cone-beam projection data can be sorted into parallel-beam ray-sums in the transverse plane while maintaining the cone angle, or data can be left as is with fan-beam rays in the transverse plane. The device advantageously uses the sorting to further increase the helical pitch and thus scanning speed.

The device also preferably uses a minimal set of projection data that satisfies the completeness condition to increase the helical pitch. A full set of projection data may also be used.

The above and other objects are also achieved by an x-ray computed tomography method including a step of performing backprojection where pixels in image reconstruction have a backprojection range. Each pixel may have its own back projection range. The back projection range may be determined using a completeness condition. The completeness condition is preferably a two-dimensional "weak" completeness condition where every line through a reconstructed slice of an image must intercept the projection of a source orbit onto the plane of the slice. Using these conditions a larger helical pitch can be achieved while maintaining image quality.

The method according to the invention is preferably applied to cone-beam geometry. Cone-beam projection data is produced by scanning a cone-beam. The method may include sorting the cone-beam projection data into parallel-beam ray-sums in the transverse plane while maintaining the cone angle, or data can be left as is with fan-beam rays in the transverse plane. The sorting is advantageously used to further increase the helical pitch and thus increase scanning speed and reduce scanning time.

The method also preferably uses a minimal set of projection data that satisfies the completeness condition to increase the helical pitch. A full set of projection data may also be used.

BRIEF DESCRIPTION OF THE INVENTION

A more complete appreciation of the invention and many of the attendant advantages thereof will be readily obtained as the same becomes better understood by reference to the following detailed description when considered in connection with the accompanying drawings, wherein:

FIG. 6A is a map of angular views available to regions of a slice;

FIG. 7 is a map of a reconstructed slice using a prior art reconstruction algorithm clipped at the weak completeness condition but including the condition of consistent back-projection;

FIG. 8 is a map of a reconstructed slice the values $\beta'_1(x,y)$-top entry and $\beta'_2(x,y)$-bottom entry;

FIG. 9 is a map of a reconstructed slice representing the data usage for the minimally required data set for the same parameters as in FIG. 6A for the IHCB algorithm;

Figure 11:
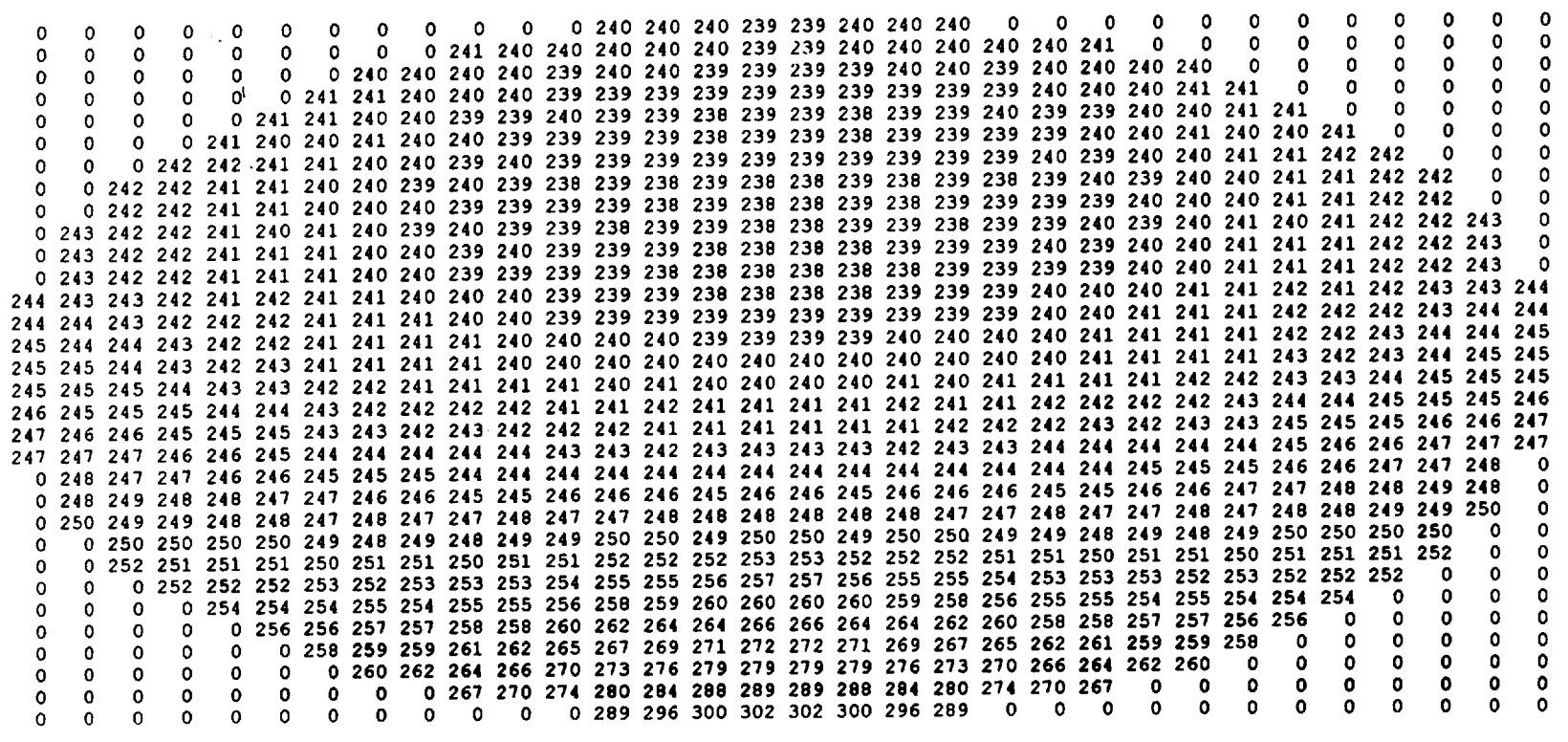
Figure 15:
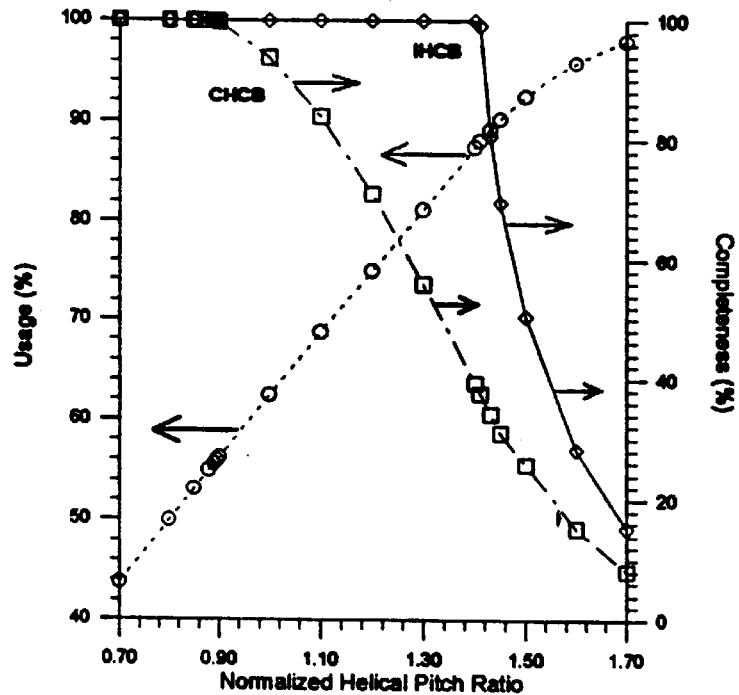
Figure 16:
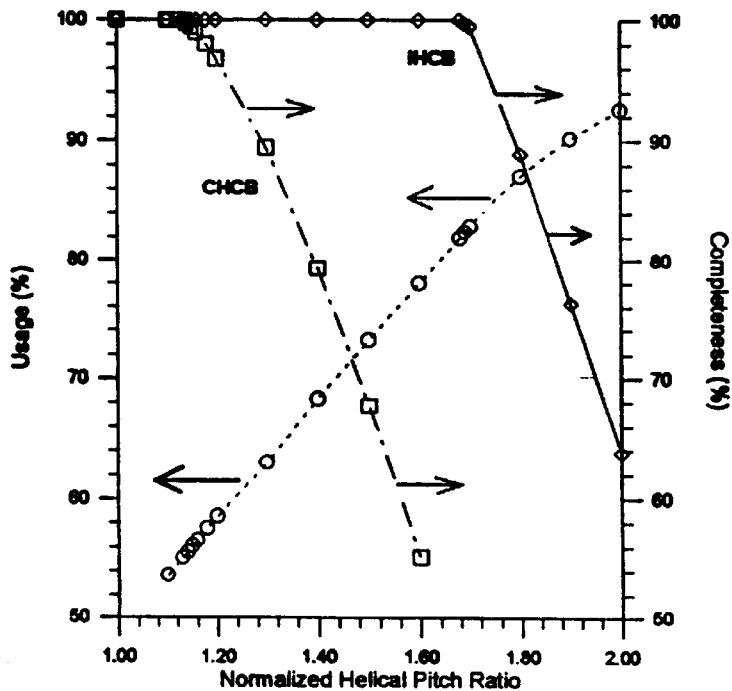
Figure 17:
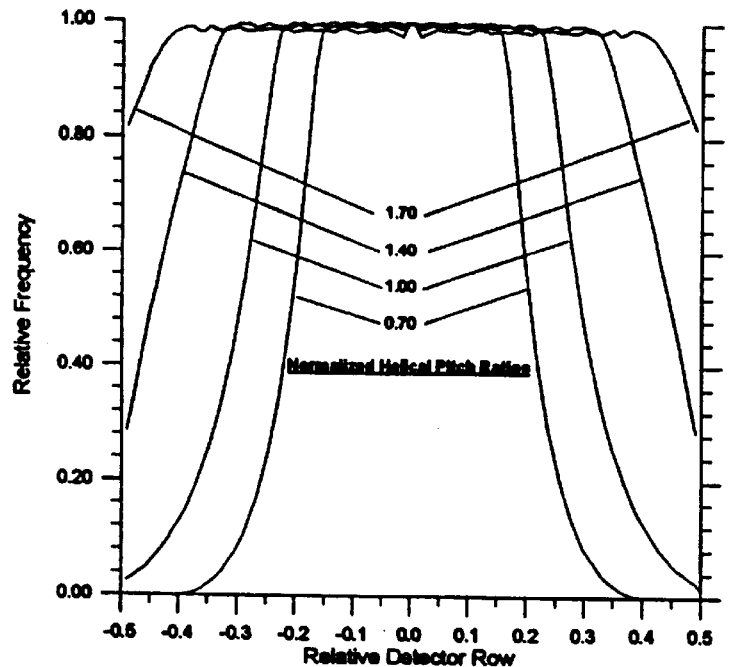
Figure 18:
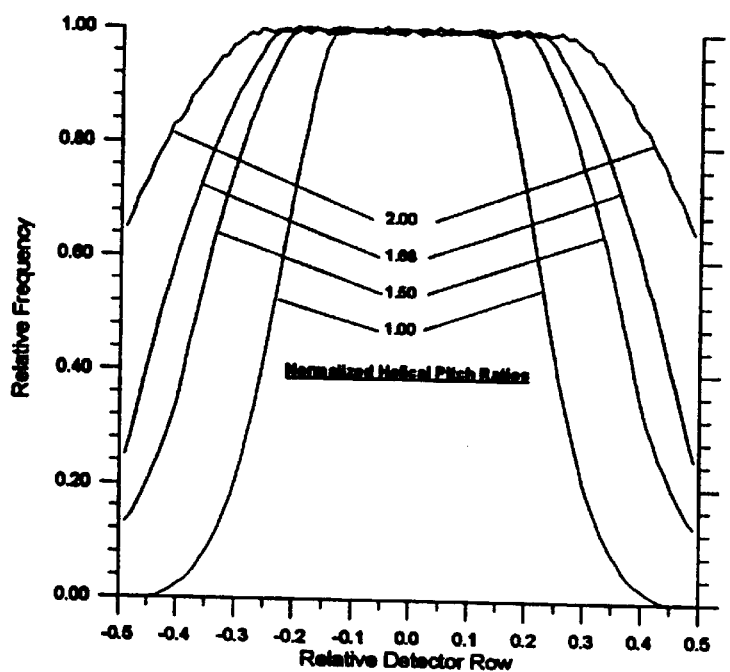

FIG. 11 presents a map for a reconstructed slice where the location in the map represents an (x,y) position and the map value is $\theta'_2(x,y) - \theta'_1(x,y)$;

Figure 12:
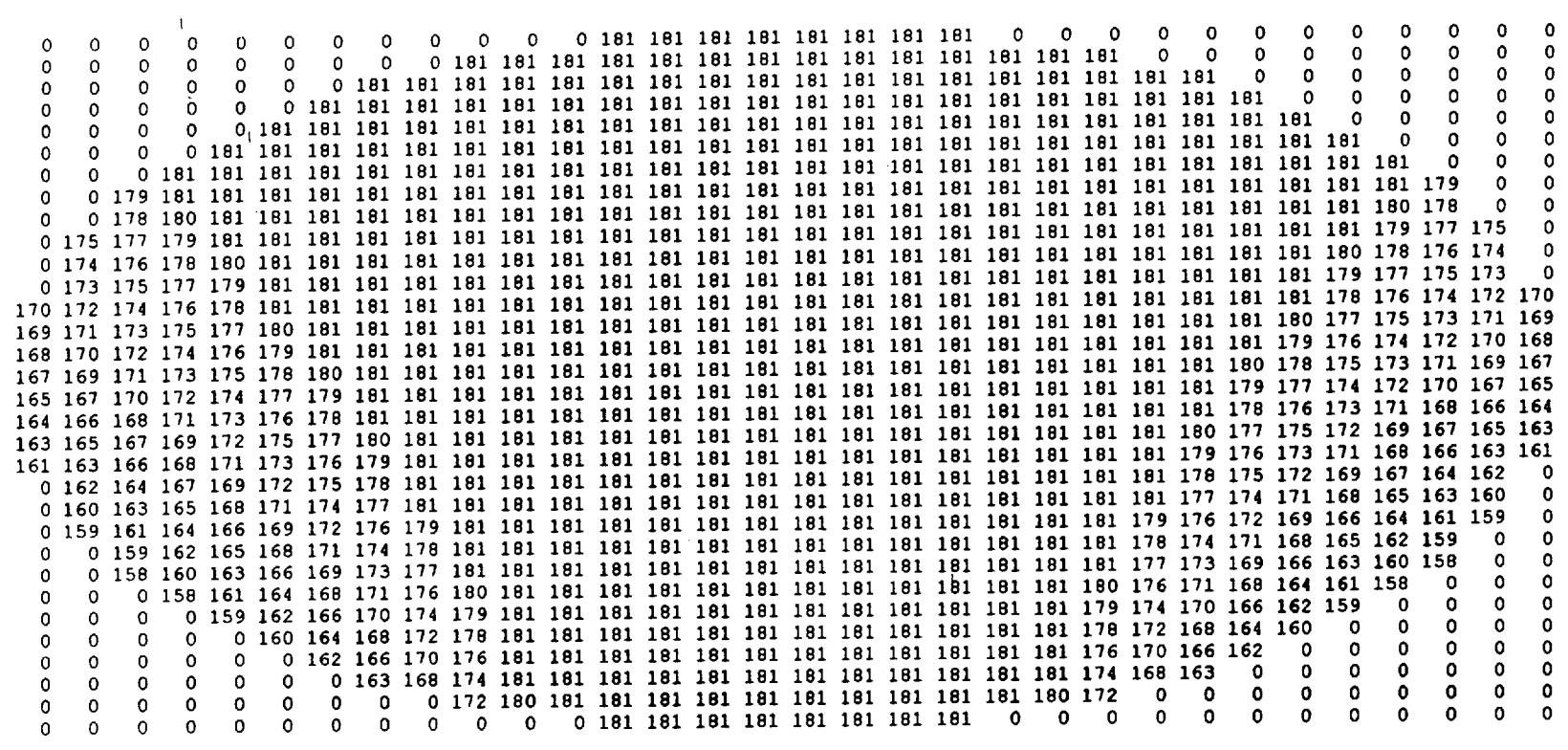

FIG. 12 is a map of $\theta'_2(x,y) - \theta'_1(x,y)$ clipped at the weak completeness condition;

Figure 13:
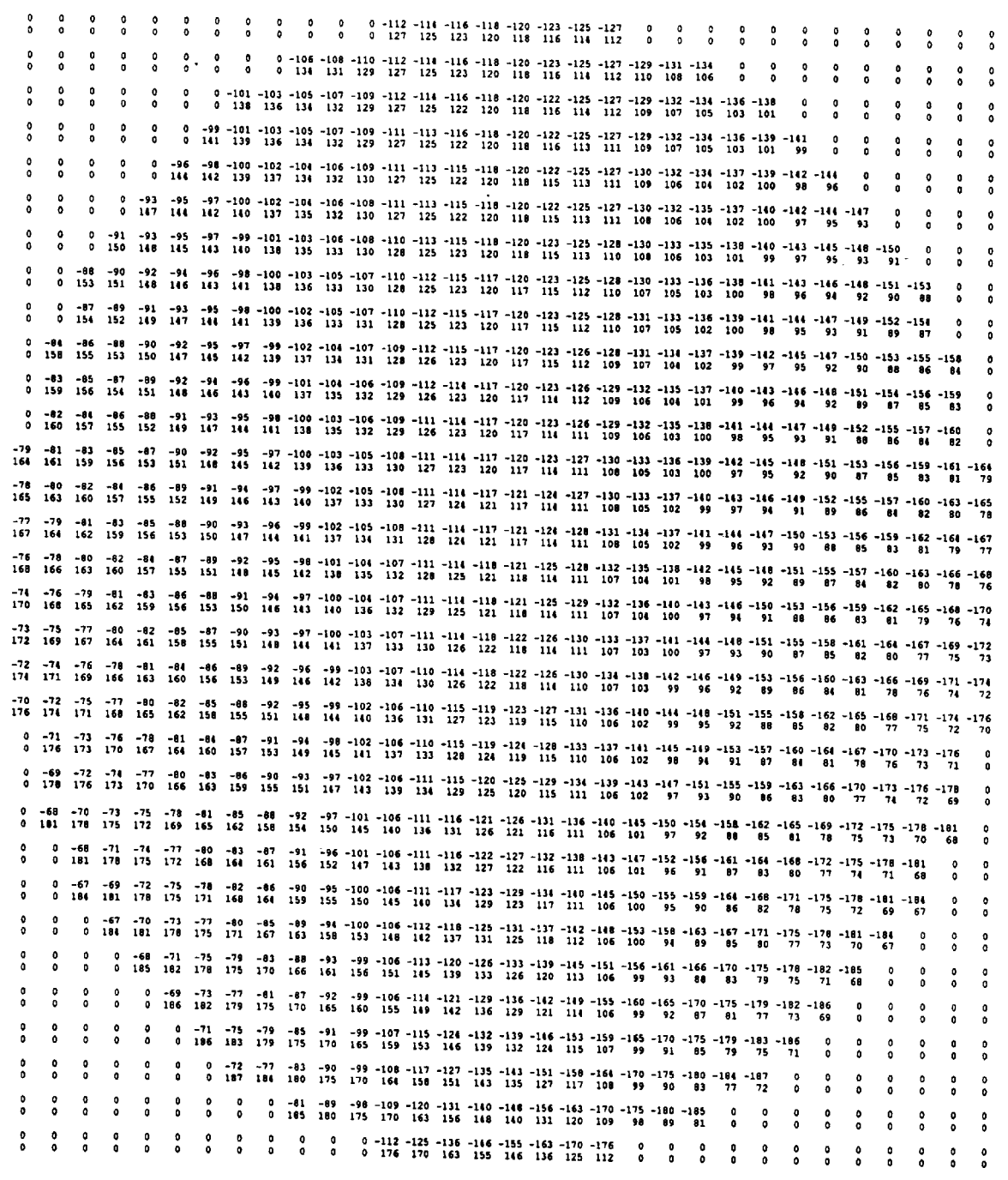

FIG. 13 is a map of the values $\theta'_1(x,y)$-top entry and $\theta'_{22}(x,y)$-bottom entry;

Figure 14:
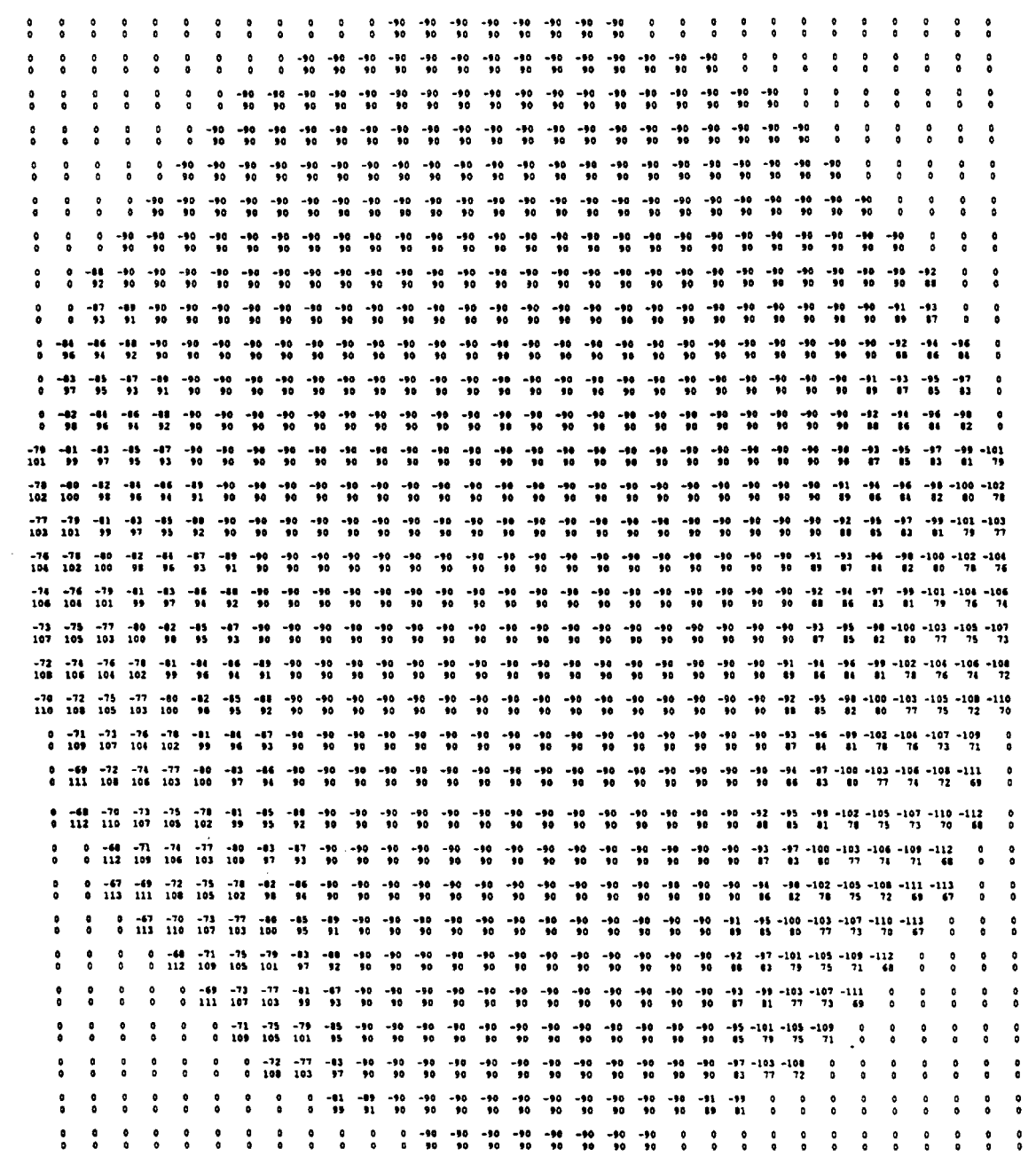

FIG. 14 a map of the values $\theta_1(x,y)$-top entry and $\theta_2(x,y)$-bottom entry;

FIG. 15 is a graph of the percentage of reconstructed image pixels that obeys the weak completeness condition and the percentage of data usage for an embodiment of the method according to the invention;

FIG. 16 is a graph of the percentage of reconstructed image pixels that obeys the weak completeness condition and the percentage of data usage for another embodiment of the method according to the invention;

FIG. 17 is a frequency histogram of ray-sum usage for an embodiment of the method according to the invention; and FIG. 18 is a frequency histogram of ray-sum usage for another embodiment of the method according to the invention.

DESCRIPTION OF THE PREFERRED EMBODIMENTS

Figure 1:
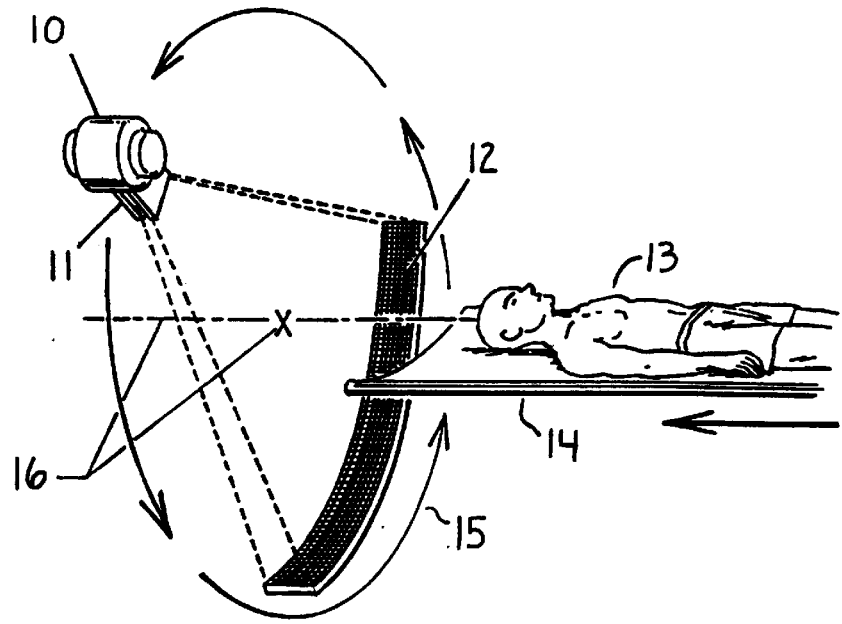
FIG. 1 is a diagram of a conventional helical x-ray computed tomography device.

Referring now to the drawings, where like reference numerals designate corresponding parts throughout the drawings, an x-ray computed tomography (CT) device and method according to the present invention will be described. As shown in FIG. 1, an x-ray tube 10 and detector 12 is rotated circularly around an object to be imaged, such as patient 13. X-ray tube 10 and detector 12 are typically arranged in a gantry and rotated using a slip-ring mechanism. A collimator 11 may be used to shape the x-ray beam emitted from x-ray tube 10. Patient 13 is situated such that the center of rotation passes through approximately its cross-sectional center, although this is not a necessary condition. While tube 10 and detector 12 are being rotated, the patient bed 14 is translated, producing a helical path of tube 10 and detector 12 around patient 13.

Figure 2:
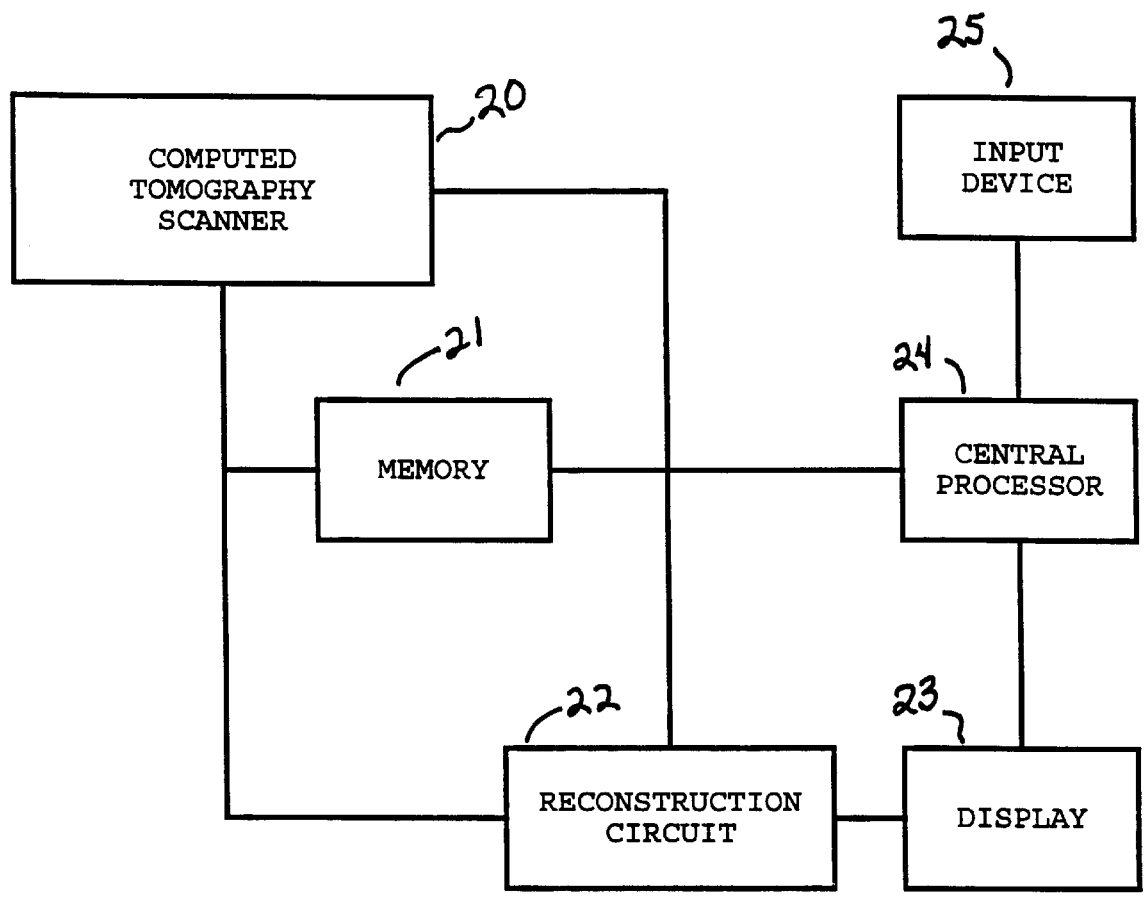
FIG. 2 is a diagram of the system according to the invention.

FIG. 2 is a diagram of the system according to the invention. A CT scanner 20 having, for example, the elements described above in connection with FIG. 1, scans an object and produces projection data, preferably cone-beam projection data, which can be stored in memory 21. The image data is fed to reconstruction circuit 22 either from scanner 20 or memory 21. Reconstruction circuit 22 reconstructs a slice or slices of the object from the image data and can use memory 21 to store intermediate or final results. The reconstructed data can be displayed on display 23, which may be a video terminal.

The elements of the system are controlled by central processor 24 using information input from input device 25, which may be a keyboard and/or mouse. Central processor 24 may be a specially designed microprocessor or a computer with software designed to operate and control the system. An operator typically uses input device 25 to enter the parameters to control the scanner and scanning operation, parameters to control the reconstruction circuit and reconstruction process, and parameters to control the display of information. Much of the operating parameters may be previously designed in the operating software, allowing the user to select predetermined scanning and reconstruction parameter sets.

Figure 3:
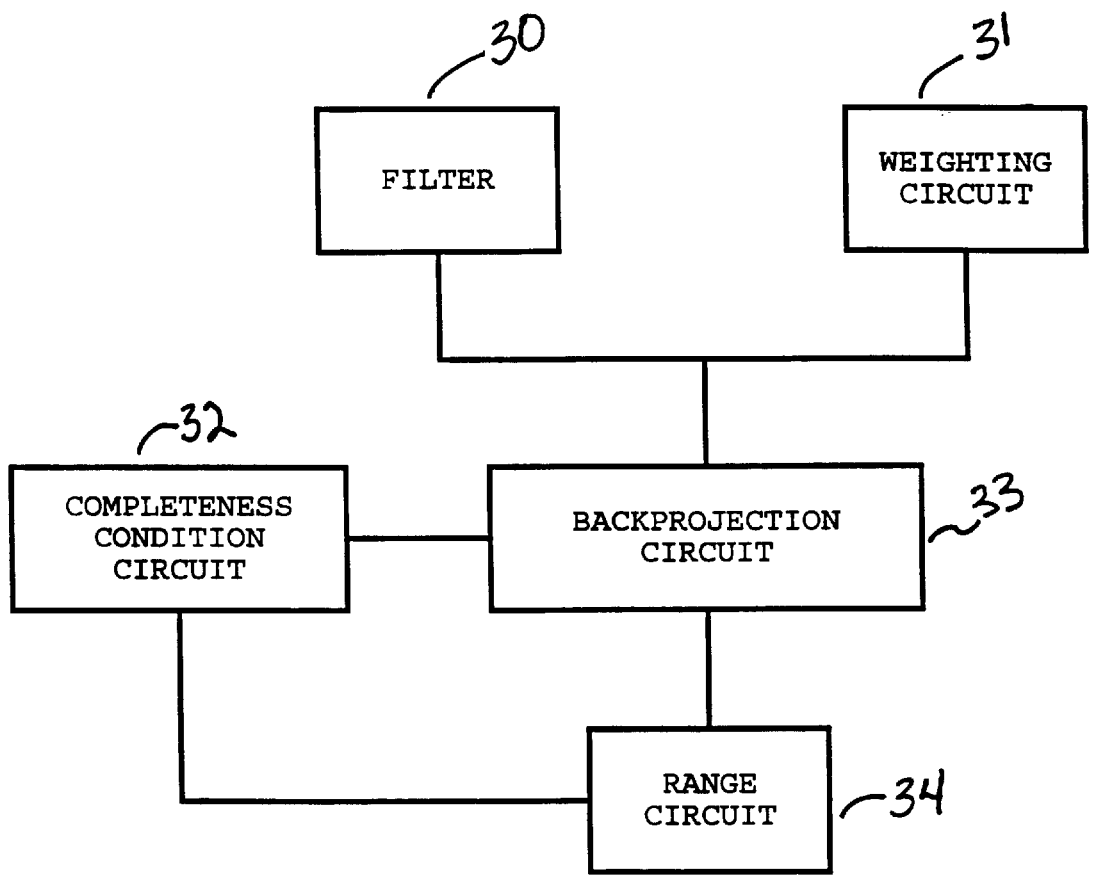
FIG. 3 is a diagram of the reconstruction circuit according to the invention.

FIG. 3 is a block diagram of reconstruction circuit 22. A backprojection circuit 33 performs a back projection operation using inputs from a filter 30, weighting circuit 31, completeness condition circuit 32 and range circuit 34.

It should be noted that the circuits of FIGS. 2 and 3 may also be implemented in software on a general purpose computer or on a programmed microprocessor. Also, the software could be run, for example, by the central processor (such as 24).

The operation of reconstruction circuit 22 will now be described. Parameters of the system can be defined as follows:

v   the constant velocity of the patient couch,
T   the rotation period of the gantry,
w   the nominal slice width: the axial aperture of a single element of the detector array, and the helical pitch ratio, $r_H$, is given by $$r_H = vT/w, \quad (1)$$

the ratio of the helical pitch (the translation of the patient couch per gantry revolution) to the projected axial aperture of a detector element. It is also possible to define a normalized helical pitch ratio, $r'_H$, defined by the helical pitch divided by the full axial length of the detector array (projected at rotation center):

$$r'_H/N = vT/Nw' \quad (2)$$

where N is the number of rows in the detector array. Here, it is assumed that two-dimensional detector array forms a section of a cylinder, focused on the x-ray source, although this is not necessary. The equations below should be modified if the detector were flat, for example.

For this three-dimensional scanning geometry, the question of mathematical completeness of the Radon space may be ignored. Instead a two-dimensional ("weak") completeness condition may be used as a guide as to when image quality—the relative absence of artifacts—can be expected to be adequate. That is, the three-dimensional completeness condition that every plane that intercepts the scanned object must also intercept the source orbit is replaced by the condition that every line through a reconstructed slice must intercept the projection of the source orbit onto the plane of the slice.

The use of the two-dimensional completeness condition to estimate a maximum helical pitch where the image quality is adequate, at least, for example, for screening where patient throughout is of prime importance and CT-angiography where the short scan times reduce susceptibility to patient motion artifacts and expand the scope for dynamic studies. A sort to parallel-beam in the transverse plane allows a higher helical pitch ratio than without the sort without violating the two-dimensional completeness condition because it requires less of the Radon space for reconstruction.

Figure 4:
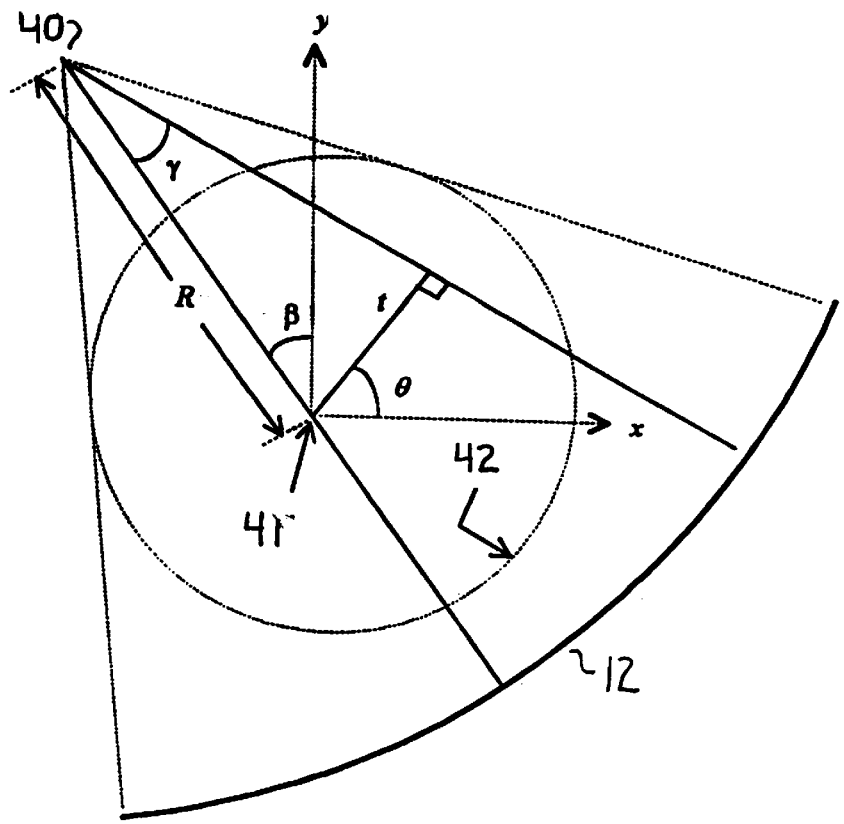
FIG. 4 is a diagram of the transverse plane in cone-beam geometry used to illustrate reconstruction according to the invention.

FIG. 4 illustrates the transverse plane in cone-beam geometry. The distance from x-ray source at a focal point 40 to a rotation center 41 in field-of-view 42 is given as R. For a fan-beam representation, $2\gamma$ is the width of the fan-beam of x-rays striking detector 12 and $\beta$ is the angle between the y-axis and a ray of the fan beam through rotation center 41. For a parallel-beam representation, $\theta$ and t variables, as shown, are used.

The analysis can be performed in two ways. The cone-beam projection data can be sorted into parallel-beam ray-sums in the transverse plane while maintaining the cone angle, or data can be left as is with fan-beam rays in the transverse plane. Referring to FIG. 4, this means either using the $\theta$, t variables for the parallel-beam representation or the original $\beta$, $\gamma$ variables for the fan-beam representation. The equations for going from the divergent projections, $p(\beta,\gamma, n)$, to semi-parallel projections, $p(\theta, t, n')$, where $n^{()}$ is the detector row index are given by:

$$\theta = \beta + \gamma \quad (3a)$$

$$t = R \sin \gamma \quad (3b)$$

$$n' = n - (\gamma/2\pi) r_H \quad (3c)$$

The third equation represents the detector row shift due to patient translation that occurs among the different t-ray-sums for a given view $\theta$.

Embodiments of the reconstruction algorithm, hereinafter referred to as IHCB, which stands for Inconsistent, Helical, Cone-Beam reconstruction, are now described. There are four embodiments, using either the parallel or fan beams with either full or minimal data. A full data set is where every beam that strikes a pixel is used in the reconstruction. Before discussing the reconstruction algorithms, it should be noted that a given cross-sectional slice in helical, cone-beam CT is continuously irradiated as it translates through the rotating cone beam, at times receiving radiation from large cone angles and at other times from the midplane of the cone. From an image quality standpoint, all slices from such a scanner are equivalent. Only a single slice need be considered (unlike from a non-helical cone-beam scanner).

First, fan-beam versions of IHCB without sort will be described. In the reconstruction algorithm according to a first embodiment, using a minimal data set, reconstruction circuit 22 implements a modified helical, Feldkamp algorithm to allow each pixel its own backprojection range while insisting on proper three-dimensional backprojection:

$$f_i(x, y) = \quad (4)$$

$$\frac{1}{\pi} \int_{\beta_1(x,y)}^{\beta_2(x,y)} \frac{1}{L^2(\beta,x,y)} \int_{-\gamma_m}^{\gamma_m} W(\beta, \gamma', x, y) p(\beta, \gamma', n) g(\gamma - \gamma', n) d\gamma' d\beta$$

$$\gamma = \tan^{-1} \frac{x\cos\beta + y\sin\beta}{R + x\sin\beta - y\cos\beta}, \quad (5a)$$

$$n = \frac{\beta}{2\pi} \frac{Rr_H}{L(\beta, x, y)}, \quad (5b)$$

-continued $$L^2(\beta, x, y) = (R\sin\beta + x)^2 + (R\cos\beta - y)^2, \quad (5c)$$

$g(\gamma - \gamma', n)$ is the convolution filter with optional row weighting, and
$W(\beta, \gamma', x, y)$ are the weights, such as Parker-like, discussed below. Filter circuit 30 and weighting circuit 31 implement the filtering weighting operations for use with the back projection algorithm. The weights or weighting scheme used can be changed according to user requirements. Circuit 34 determines the back projection range for each pixel.

The inconsistent backprojection means that each pixel, (x,y), has its own backprojection range as indicated by the $\beta_1(x,y)$ and $\beta_2(x,y)$ as functions on the limits on the back-projection integral. The limits on the integral depend on x and y, as opposed to prior art reconstruction methods where there is no x,y dependence. The angular range of source positions, or views, designated by angle A, that contain a ray path from the focal spot of the $$\left| \frac{\beta}{2\pi} - \frac{Rr'_H}{L(\beta, x, y)} \right| \leq \frac{1}{2} \quad (6)$$

is satisfied. $\beta'_1(x,y)$ and $\beta'_2(x,y)$ are given by the roots of equation (6) made into an equality:

$$F(\beta'(x, y)) = \frac{\beta}{2\pi} - \frac{Rr'_H}{L(\beta, x, y)} \pm \frac{1}{2} = 0. \quad (7)$$

Figure 5:
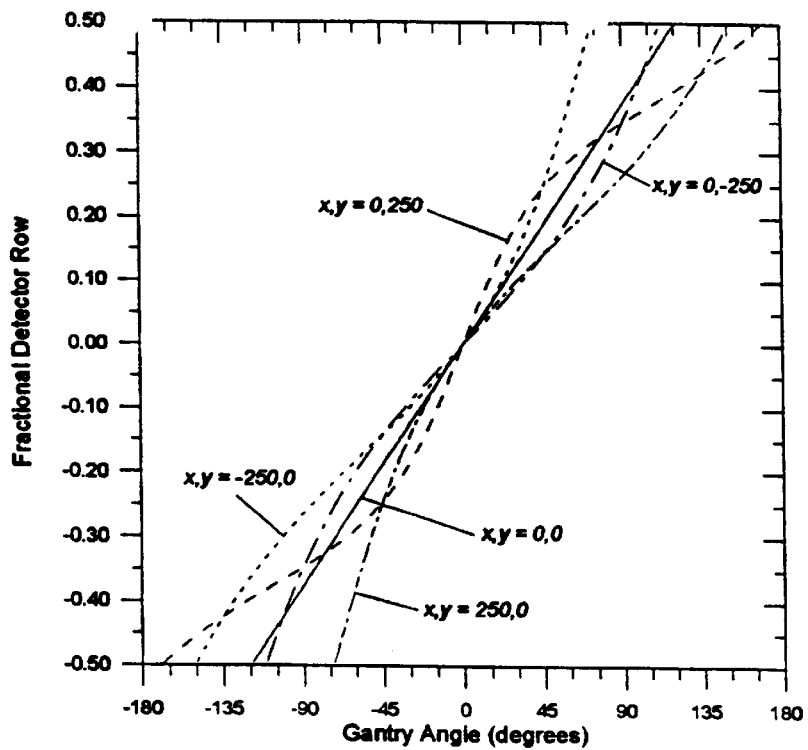
FIG. 5 is a diagram of trajectories of selected pixels.

FIG. 5 shows the trajectories of ray-sums through the rows of the detector array for selected pixels as a function of $\beta$. In this example, the pixels are at rotation center, and the north-, south-, east- and west-most extremes for a field of view of 500 mm, R=600 mm and $r'_H$=1.5. The gantry angles where a curve leaves the detector array (crosses the fractional detector row $\pm\frac{1}{2}$) are the $\beta'_{1,2}$ for that pixel.

The minimal data set necessary to give an adequate quality image according to the weak completeness condition is determined by circuit 32 for use in the backprojection algorithm. This means that the actual backprojection limits are restricted to $$\beta_2(x,y) - \beta_1(x,y) = \pi 2\gamma_m \forall x, y, \quad (8)$$

where $2\gamma_m$ is the fan angle in the transverse plane. Therefore, to satisfy the weak completeness condition, $$\beta'_2(x,y) - \beta'_1(x,y) \geq \pi + 2\gamma_m \forall x, y. \quad (9)$$

$\beta_1$ and $\beta_2$ then fall within the inclusive $\beta'_1,\beta'_2$ interval such that $\frac{1}{2}(\beta_1+\beta_2)$ is as close to 0 as possible while satisfying equation (8).

Figure 6A:
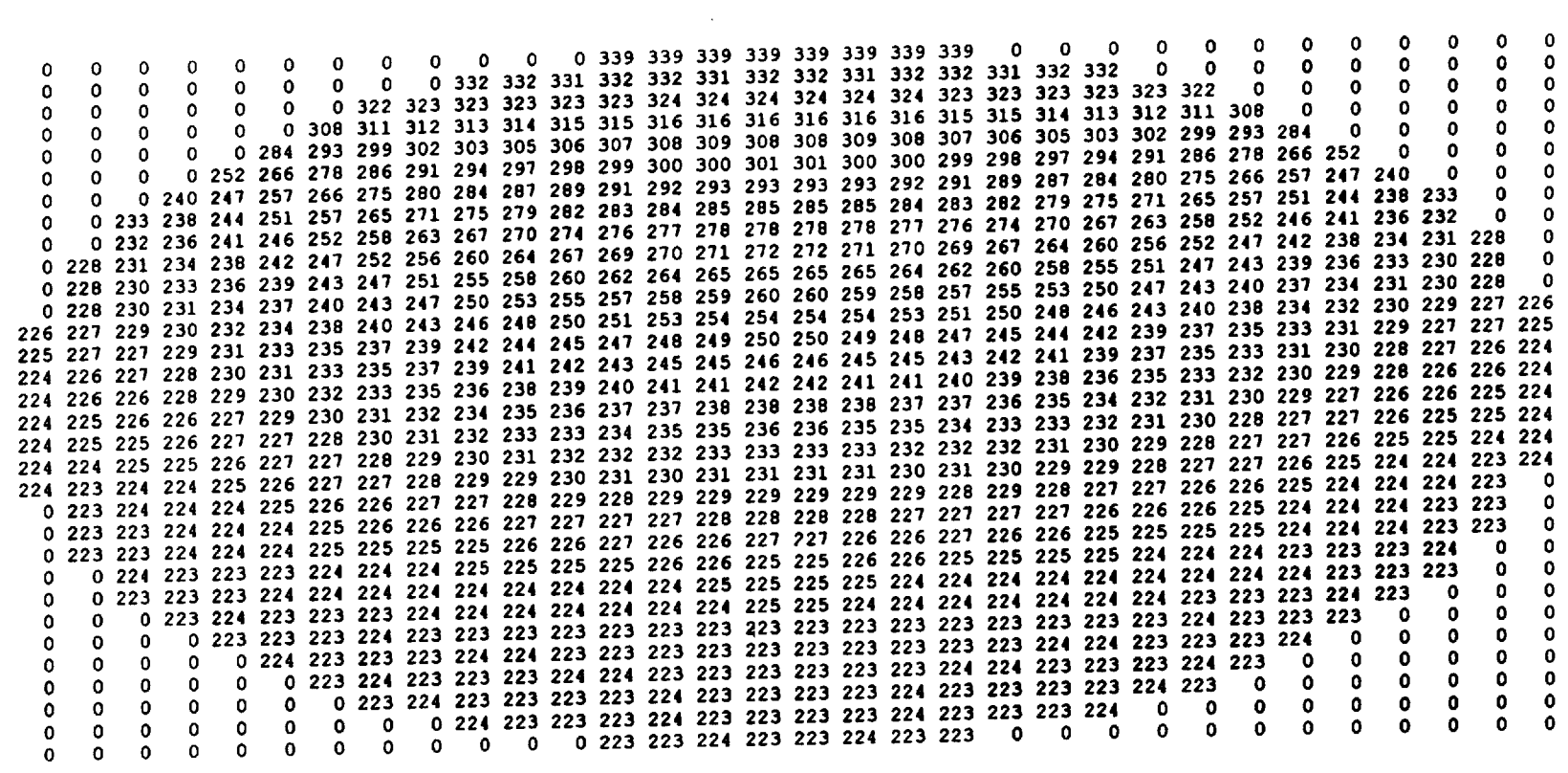
Figure 6B:
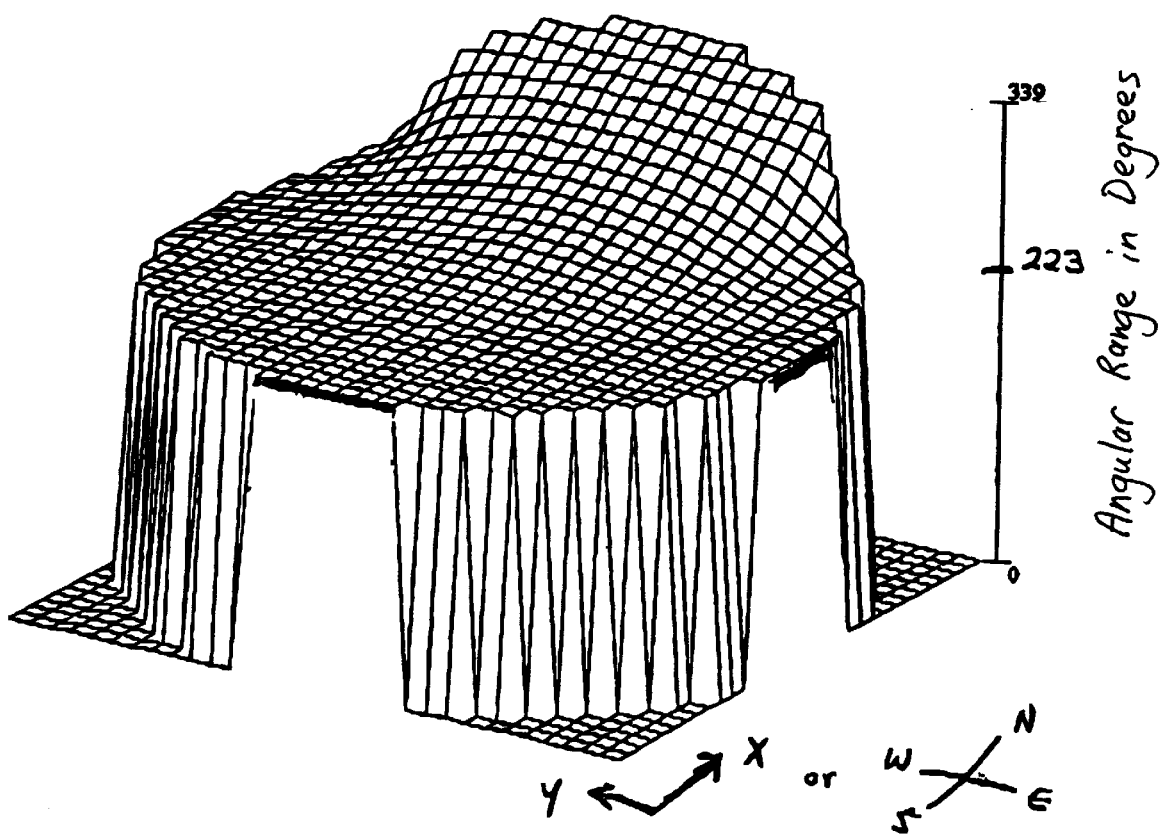
FIG. 6B is a three-dimensional representation of the map of FIG. 6A.

FIGS. 6A and 6B are examples of a map for a reconstructed slice, based upon a 32×32 reconstruction matrix, where the location in the map represents an (x,y) position in the image and the map values are $\beta'_2(x,y)-\beta'_1(x,y)$. The numbers represent the range in degrees that the region of the slice is in the cone beam. For example, the north-most pixel is in the cone beam for 339° while the south-most pixel is in the cone beam for 223°. The data was generated for a normalized helical pitch of 1.5, R=600 mm, a field of view having a diameter of 500 mm and a reconstruction radius of 250 mm.

Figure 7:
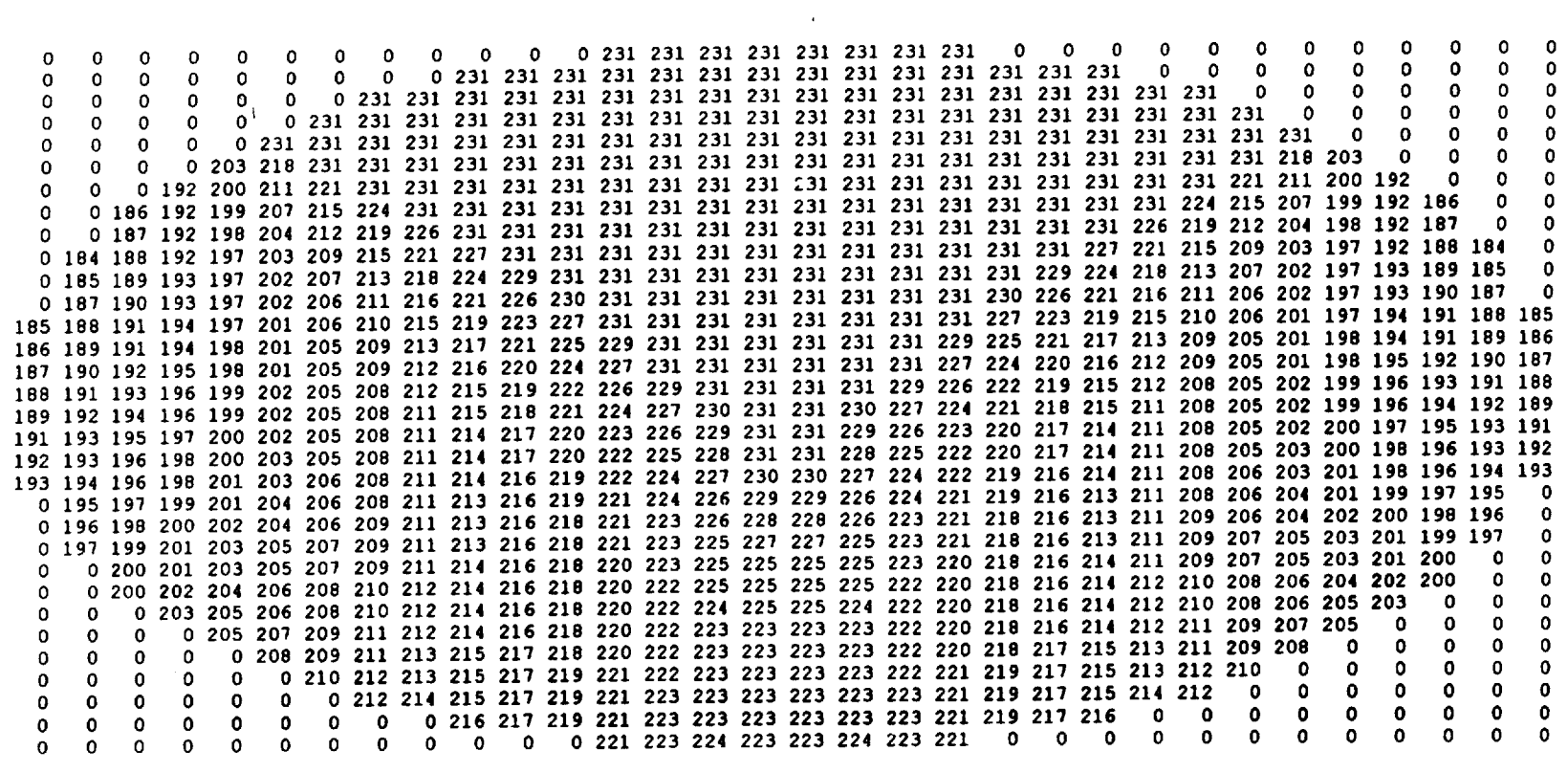

FIG. 7 is a map of a reconstructed slice using a prior art reconstruction algorithm (consistent, helical cone beam without sorting the data) with $\beta'_2(x,y)$ and $\beta'_1(x,y)$ clipped at the weak completeness condition of $\pi+2\gamma_m$ but including the condition of consistent backprojection: $\beta'_1(x,y) \geq -(\pi/2+\gamma_m)$ and $\beta'_2(x,y) \leq (\pi/2+\gamma_m)$. The data was prepared using the same conditions described for FIG. 6A. In this example, each pixel must be in the slice for −115° to 115° (±½[180°+ 50° fan angle]) in order to satisfy the weak completeness condition. Thus, any entry in FIG. 7 that is less than π+2γ$_m$ implies that the location cannot be reconstructed with a consistent, complete (weak completeness condition) data set. Only 26% of the pixels meet the completeness condition (it is noted that the value 231 is due to computer quantization to integer angles, including both of ±215°). On the other hand, as long as the entries in FIG. 6A are greater than π+2γ$_m$, then an inconsistent backprojection is possible that satisfies the weak completeness condition.

Figure 8:
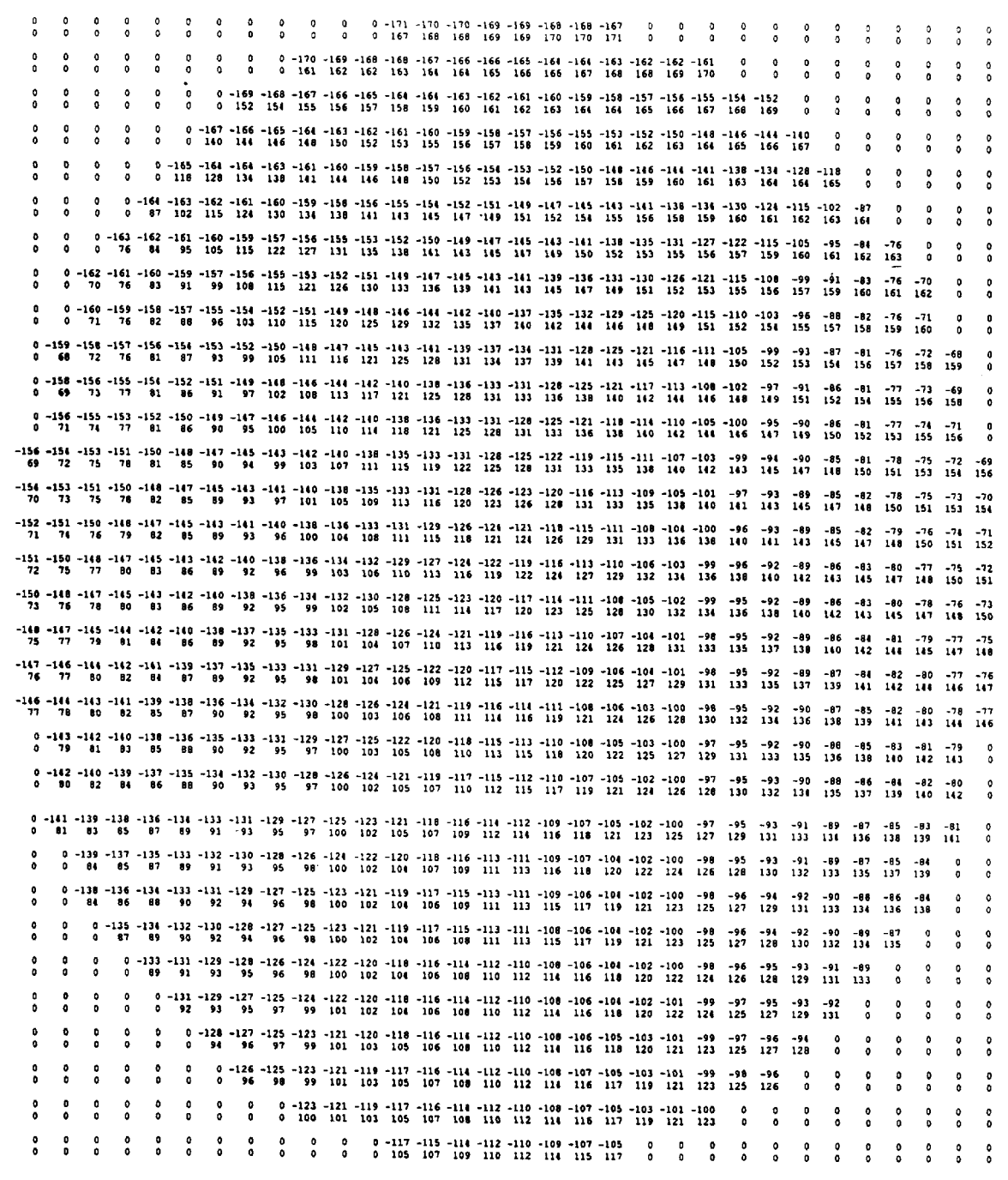

FIG. 8 is the map for the values β'$_1$(x,y)-top entry and β'$_2$(x,y)-bottom entry. The top entry is the first gantry angle irradiated while the bottom is the last gantry angle irradiated. The difference between the first and last angles is the range shown in FIG. 6A.

Figure 9:
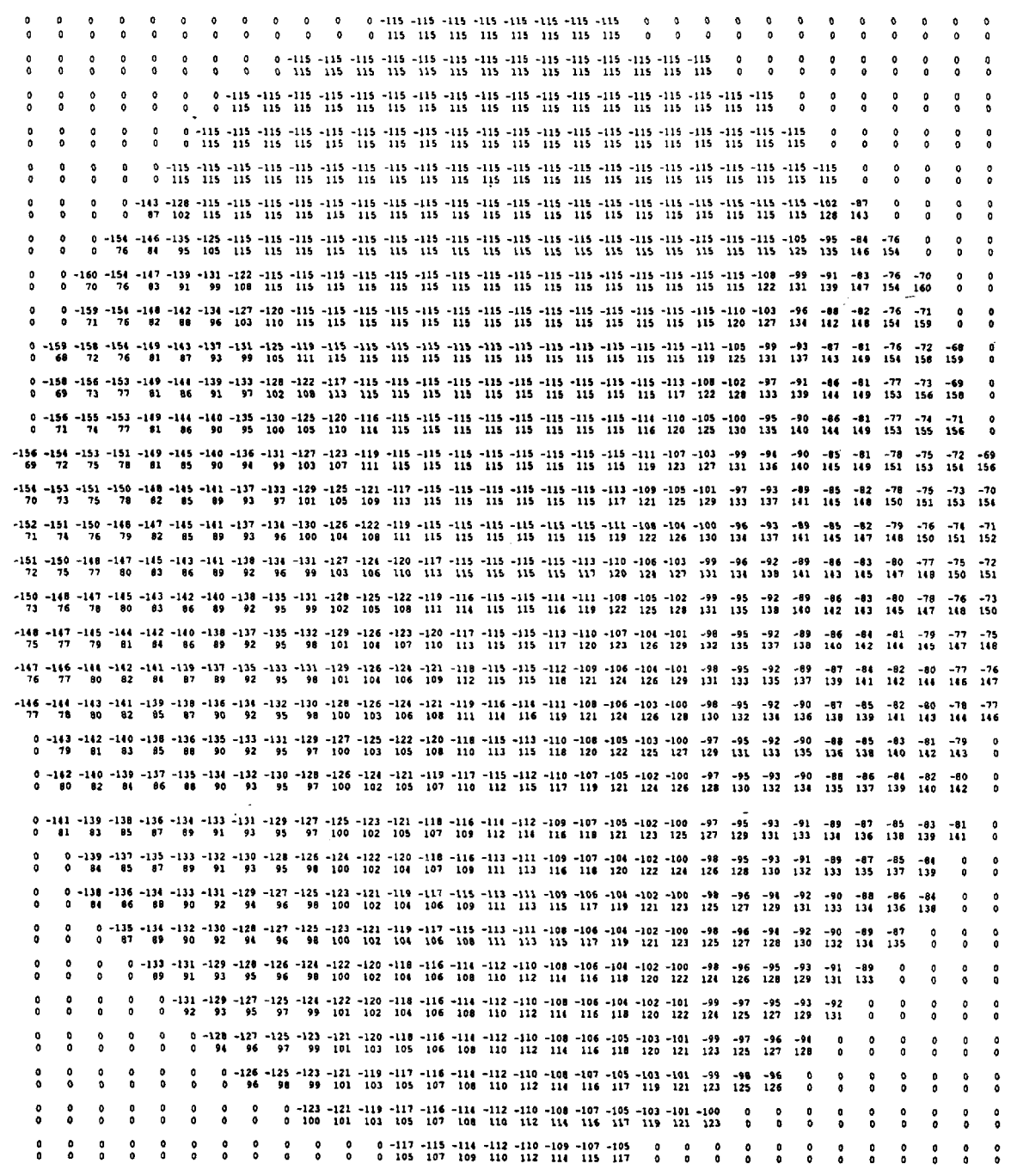

FIG. 9 is the map for the values β$_1$(x,y)-top entry and β$_2$(x,y)-bottom entry. This map represents the data usage for the minimally required data set for the same parameters as in FIG. 6A for the IHCB algorithm, where each pixel has its own backprojection range. About 50% of the slice satisfies the weak completeness condition (the difference between the first and last angles is 180° plus the fan angle (230°)).

Equations (4) and (5) assume that the gantry angle is reset for each slice so that the view at β=0 has the focal spot in the slice plane. Thus, if the algorithm is implemented as written, each slice is rotated with respect to its neighbor by 2πΔz/vT, where Δz is the axial pitch between slices. In order to have the slices come out with the correct angular orientation, the actual β, or absolute β, is used everywhere in equations (4) and (5) except in the numerator of equation (5b), which still uses the relative β and for the condition that ½(β$_1$+β$_2$) be as close to 0 as possible.

Equation (4) can be tedious to implement, when Parker-like weights, which prevent overcounting, are used. The Parker-like weights are different for each pixel and thus each pixel requires its own convolved data set. In second and third embodiments, the invention applies a sort to parallel rays in the transverse plane. Parker-like weights do not enter into this analysis. Here, the reconstruction algorithm is as follows:

$$f_i(x,y) = \frac{1}{\pi} \int_{\theta_1(x,y)}^{\theta_2(x,y)} \omega(\theta,x,y) \int_{-\infty}^{\infty} p(\theta,t',n')g(t-t',n')dt'd\theta \quad (10)$$

where: $f_i(x,y)$ is the reconstructed pixel at location x,y for slice i, $$t = x\cos\theta + y\sin\theta, \quad (11a)$$

$$n' = \frac{\theta}{2\pi} \frac{r_H \cos\gamma}{U(\theta,x,y)}, \quad (11b)$$

$$U(\theta,x,y) = 1 - \frac{x\sin\theta}{R} + \frac{y\cos\theta}{R}, \quad (11c)$$

g(t−t',n') is the convolution filter with optional row weighting, and

ω(θ,x,y) is a weight or interpolation function.

As before, the inconsistent backprojection means that each pixel, x,y, has its own backprojection range as indicated by θ$_1$(x,y) and θ$_2$(x,y) as functions on the limits on the backprojection integral. The angular range of two-dimensional projections, or views, designated by angle θ, that contain a ray path from the focal spot of the source through the pixel at x,y to the detector array is given when the inequality $$\left| \frac{\theta}{2\pi} - \frac{r_H \cos\gamma}{U(\theta,x,y)} + \frac{\gamma r_H}{2\pi} \right| \leq \frac{1}{2} \quad (12)$$

is satisfied. Equation (3c) is used to refer back to the original detector rows. θ'$_1$(x,y) and θ'$_2$(x,y) are given by the roots of the above made into an equality:

$$F(\theta'(x,y)) = \frac{\theta}{2\pi} - \frac{r_H \cos\gamma}{U(\theta,x,y)} + \frac{\gamma r_H}{2\pi} \pm \frac{1}{2} = 0. \quad (13)$$

Figure 10:
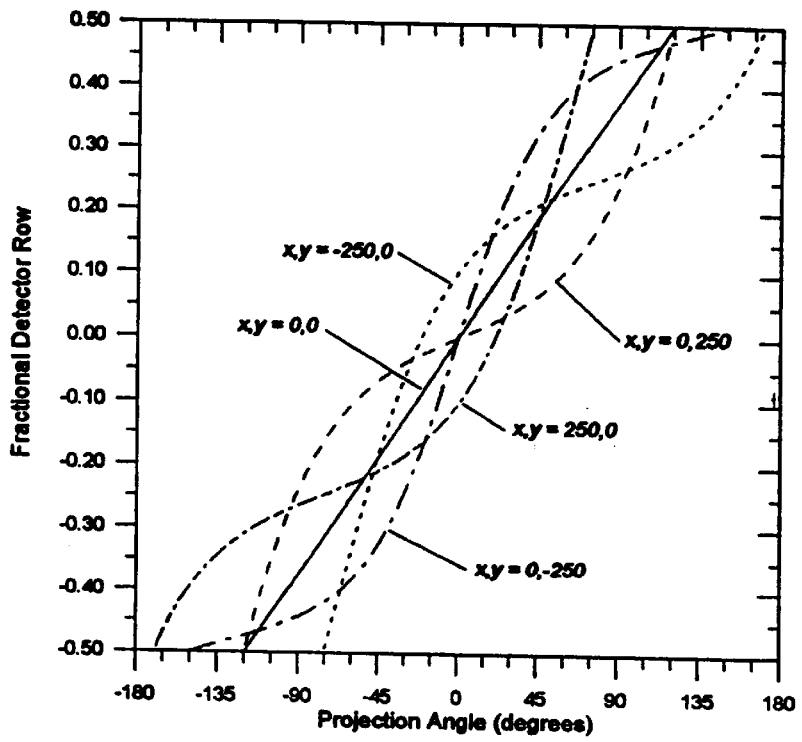
FIG. 10 shows the trajectories of ray-sums through the rows of a detector array for selected pixels as a function of $\theta$.

FIG. 10 shows the trajectories of ray-sums through the rows of the detector array for selected pixels as a function of θ. Similar to FIG. 5, trajectories are given for the north-, south-, east- and west-most pixels after the sort to parallel beam in the transverse plane. The projection angles where a curve leaves the detector array (crosses the fractional detector row ±½) are the θ'$_{1,2}$ for that pixel.

In the second embodiment the minimal data set necessary to give an adequate quality image according to the weak completeness condition is determined and utilized. That means that the actual backprojection limits are restricted to $$\theta_2(x,y) - \theta_1(x,y) = \pi \forall x,y, \quad (14)$$

Therefore, to satisfy the weak completeness condition, $$\theta'_2(x,y) - \theta'_1(x,y) \geq \pi \forall x,y. \quad (15)$$

θ$_1$ and θ$_2$ then fall within the inclusive θ'$_1$, θ'$_2$ interval such that ½(θ$_1$+θ$_2$) is as close to 0 as possible while satisfying Equation (14). FIG. 11 presents a map for a reconstructed slice where the location in the map represents an (x,y) position and the map value is θ'$_2$(x,y)−θ'$_1$(x,y). FIG. 12 is a map of θ'$_2$(x,y)−θ'$_1$(x,y) clipped at the weak completeness condition of π but including the condition of consistent backprojection: θ'$_1$(x,y)>−π/2 and θ'$_2$(x,y)<π/2. Thus any entry in FIG. 12 that is less than n implies that the location cannot be reconstructed with a consistent, complete (weak completeness condition) data set. On the other hand, as long as the entries in FIG. 11 are greater than π, then an inconsistent backprojection is possible that satisfies the weak completeness condition.

FIG. 13 is the map for the values θ'$_1$(x,y)-top entry and θ'$_2$(x,y)-bottom entry. FIG. 14 is the map for the values θ$_1$(x,y)-top entry and θ$_2$(x,y)-bottom entry. The weight function ω can be ignored (set to unity).

In the third embodiment, where all the available data is used, then the backprojection range sets θ$_1$(x,y)=θ'$_1$(x,y) and θ$_2$(x,y)=θ'$_2$(x,y) and the weight function ω is introduced. Equivalently, projection data can be averaged using the weight conditions listed below before convolution/backprojection and then use the minimal data backprojection limits. Because most pixels have a θ-coverage greater than 180°, then the weight function must obey $$\sum_k \omega(\theta + k\pi, x, y) = 1, \quad (16)$$

where k is an integer such that $$\theta'_1(x,y) \leq \theta(x,y) + k\pi \leq \theta'_2(x,y) \quad (17)$$

A distance weighted function that peaks for θ+kπ=0 to reduce large cone-angle artifacts is preferable for ω.

The IHCB algorithm can be contrasted with a consistent, helical cone-beam reconstruction algorithm, CHCB. After the sort, the simplest CHCB algorithm does not use the weighting function and the backprojection limits are θ$_{1,2}$=π/2. However, the maximum helical pitch ratio that doesn't violate the weak completeness condition throughout the field-of-view is significantly smaller than with the IHCB approach. The table below summarizes the application limits for $r'_H$ for these reconstruction methods for the scanner parameters described in connection with FIG. 5. Notice that for $r'_H \leq 1.14$ with the sort and for $r'_H \leq 0.90$ without the sort, the IHCB and CHCB algorithms are the same.

|      | Without Sort | With Sort |
|------|--------------|-----------|
| CHCB | 0.90         | 1.14      |
| IHCB | 1.40         | 1.68      |

These values were determined for a field of view of 500 mm, R=600 mm. Different values will result from scanners having different parameters.

The above analysis can be carried further for the minimal data set cases. As a function of the helical pitch ratio, it is determined what fraction of the image satisfies the weak completeness condition and what percentage of the available data is used during image reconstruction. FIG. 15 gives the results without the sort. In FIG. 15 the right axis is the percentage of the reconstructed image that obeys the weak completeness condition. The solid line with diamonds is for the method according to the invention, and the dash-dotted line is a prior art algorithm (CHCB). The left axis is the percentage of data usage. The curve with the circles corresponds to the left axis and is for either algorithm. FIG. 16 gives the results with the sort to parallel-beam in the transverse plane. The curves and axes designations are the same as those in FIG. 15.

The highest helical pitch ratio so that all pixels obeys the weak completeness condition, 1.68 with the sort, uses 82% of the available ray-sums. A higher helical pitch ratio will utilize a greater fraction of the available data but at the expense of image quality in certain regions of the reconstructed field-of-view. A lower helical pitch ratio will give completeness and probably better image quality and narrower slice sensitivity profile but by using a lesser percentage of the available data. Of course, the third embodiment could be used for reconstruction, which, by definition, uses 100% of the data for any $r'_H$, with the same completeness curve as in FIG. 16 but probably with a wider slice sensitivity profile than with the second embodiment.

Sticking with the minimal data sets, the first (without sort) and second (with sort) embodiments, which ray-sums are used and which are not, can be determined. This turns out to be a function of which detector row a ray-sum belongs to and the helical pitch ratio. FIG. 17 (without the sort) and FIG. 18 (with the sort) show histogram distributions of the ray-sums over relative detector row for several helical pitch ratios. A histogram value of 1 means all ray-sums in that detector row are backprojected. Notice that the central portion of the area detector is fully utilized; the edges of the detector are not. This suggests a detector 12 design where the central rows of the detector have fine axial pitch while the outer rows could have cruder axial pitch. Such a design would not unduly affect the slice sensitivity profile.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by letters patent of the United States is:

1. An image reconstruction method, comprising:
   obtaining projection data of a subject; and
   backprojecting said projection data with pixels having a backprojection range.

2. A method as recited in claim 1, comprising:
   determining said backprojection range using a completeness condition.

3. A method as recited in claim 2, comprising:
   determining a minimal set of said projection data for image reconstruction based upon said completeness condition.

4. A method as recited in claim 1, comprising:
   determining said backprojection range using a completeness condition such that substantially every line through a reconstructed slice of said subject intercepts a projection of an orbit of said source on said slice.

5. A method as recited in claim 1, where said backprojecting comprises using:

$$f_i(x, y) = \frac{1}{\pi} \int_{\beta_1(x,y)}^{\beta_2(x,y)} \frac{1}{L^2(\beta, x, y)} \int_{-\gamma_m}^{\gamma_m} W(\beta, \gamma', x, y) p(\beta, \gamma', n) g(\gamma - \gamma', n) d\gamma' d\beta$$

where: $f_i(x, y)$ is a reconstructed pixel at location x, y for slice i, $$\gamma = \tan^{-1} \frac{x\cos\beta + y\sin\beta}{R + x\sin\beta - y\cos\beta},$$

$$n = \frac{\beta}{2\pi} \frac{Rr_H}{L(\beta, x, y)},$$

$$L^2(\beta, x, y) = (R\sin\beta + x)^2 + (R\cos\beta - y)^2,$$

$g(\gamma - \gamma', n)$ is a filtering function, and
$W(\beta, \gamma', x, y)$ is a weighting function.

6. A method as recited in claim 5, comprising:
   determining a minimal set of said projection data to perform said backprojection.

7. A method as recited in claim 5, comprising:
   using substantially all of said projection data to perform said backprojection.

8. A method as recited in claim 5, comprising:
   setting backprojection limits as $\beta_2(x,y) - \beta_1(x,y) = \pi + 2\gamma_m$, where $2\gamma_m$ is a fan angle of an x-ray beam used to produce said projection data.

9. A method as recited in claim 8, comprising:
   where $r'_H$ is a normalized pitch ratio, $\beta'_1(x,y)$ and $\beta'_2(x,y)$ are roots of $F(\beta'(x,y))$, and $\beta'_2(x,y) - \beta'_1(x,y) \geq \pi + 2\gamma_m$ $$F(\beta'(x, y)) = \frac{\beta}{2\pi} \frac{Rr'_H}{L(\beta, x, y)} \pm \frac{1}{2} = 0.$$

10. A method as recited in claim 1, wherein said backprojecting comprises using:

$$f_i(x, y) = \frac{1}{\pi} \int_{\theta_1(x,y)}^{\theta_2(x,y)} \omega(\theta, x, y) \int_{-\infty}^{\infty} p(\theta, t', n') g(t - t', n') dt' d\theta$$

where: $f_i(x,y)$ is a reconstructed pixel at location x,y for slice i, $t = x\cos\theta + y\sin\theta,$ $$n' = \frac{\theta}{2\pi} \frac{r_H \cos\gamma}{U(\theta, x, y)},$$

-continued $$U(\theta, x, y) = 1 - \frac{x\sin\theta}{R} + \frac{y\cos\theta}{R},$$

g(t–t',n') is a filtering function, and
ω(θ,x,y) is one of a weight or interpolation function.

11. A method as recited in claim 10, comprising:
detecting said projection data using a detector having a plurality of rows; and sorting said projection data using:

θ=β+γ;

t=R sin γ;

and n'=n−(γ/2π)$r_H$ where:
$r_H$ is a helical pitch ratio;
R is a distance from an x-ray source to a focal point;
n is an index of a detector row before sorting;
n' is an index of a detector row after sorting;
β is an angle between a y-axis and a central ray of an x-ray beam;
γ is an angle of a ray sum within a projection given by β; and
θ is a view angle after sorting with respect to an x-axis.

12. A method as recited in claim 10, comprising:
determining a minimal set of said projection data to perform said backprojection.

13. A method as recited in claim 10, comprising:
using substantially all of said projection data to perform said backprojection.

14. A method as recited in claim 10, comprising:
setting backprojection limits as $\theta_2(x,y) - \theta_1(x,y) = \pi$.

15. A method as recited in claim 14, comprising:

$$F(\theta'(x,y)) = \frac{\theta}{2\pi} - \frac{r'_H \cos\gamma}{U(\theta, x, y)} + \frac{\gamma r'_H}{2\pi} \pm \frac{1}{2} = 0$$

where $r'_H$ is a normalized pitch ratio, $\theta'_1(x,y)$ and $\theta'_2(x,y)$ are roots of $F(\theta'(x,y))$, and $\theta'_2(x,y) - \theta'_1(x,y) \geq \pi$.

16. A method as recited in claim 1, wherein said backprojecting comprises:
backprojecting said projection data with each of said pixels having respective individual back projection ranges.

17. A method as recited in claim 1, comprising:
detecting said projection data with a detector having a plurality of rows;
sorting said projection data using:

θ=β+γ;

t=R sin γ;

and n'=n−(β/2π)$r_H$;

where:
$r_H$ is a helical pitch ratio;
R is a distance from an x-ray source to a focal point;
n is an index of a detector row before sorting;
n' is an index of a detector row after sorting;
β is an angle between a y-axis and a central ray of an x-ray beam;
β is an angle of a ray sum within a projection given by β; and
θ is a view angle after sorting with respect to an x-axis.

18. A method of operating a computed tomography device, comprising:
helically scanning an object;
determining a backprojection range of pixels in a reconstructed image;
determining a helical pitch ratio using said range.

19. A method as recited in claim 18, wherein determining said ratio comprises:
determining a completeness condition;
using substantially only those pixels satisfying said condition.

20. A method as recited in claim 18, comprising:
obtaining projection data; and
sorting said projection data into parallel-beam ray-sums in a transverse plane of said scanning.

21. A method as recited in claim 18, comprising:
determining said back projection range using a completeness condition such that substantially every line through a reconstructed slice of said subject intercepts a projection of an orbit of said source on said slice.

22. A method as recited in claim 18, wherein determining said ratio comprises:
determining an amount of data used to generate said reconstructed image; and
determining an amount of said reconstructed image that satisfies a predetermined completeness condition.

23. A method as recited in claim 22, comprising:
determining said amount of said reconstructed image to be substantially all of said reconstructed image; and
using up to a corresponding maximal amount of said data.

24. A method as recited in claim 22, comprising:
determining said amount of data and said amount of reconstructed image based upon image quality.

25. A method as recited in claim 22, comprising:
determining a first helical pitch ratio corresponding to said amount of said reconstructed image determined to be substantially all of said reconstructed image and an amount of said data determined to be a corresponding maximal amount; and
increasing said first helical pitch ratio by using less than substantially all of said reconstructed image and using more that said corresponding maximal amount of said data.

26. An image reconstruction device, comprising:
a backprojection circuit;
a backprojection range circuit connected to said backprojection circuit; and
a completeness condition circuit connected to said backprojection circuit.

27. A device as recited in claim 26, wherein said completeness condition circuit comprises:
means for determining a minimal set of projection data for image reconstruction.

28. A device as recited in claim 26, wherein said completeness condition circuit comprises:
means for determining that a line through a reconstructed slice must intercept a projection of an orbit of a x-ray source onto a plane of the slice.

29. A device as recited in claim 26, wherein said back projection circuit uses:

$$f_i(x, y) = \frac{1}{\pi} \int_{\beta_1(x,y)}^{\beta_2(x,y)} \frac{1}{L^2(\beta, x, y)} \int_{-\gamma_m}^{\gamma_m} W(\beta, \gamma', x, y) p(\beta, \gamma', n) g(\gamma - \gamma', n) d\gamma' d\beta$$

where: $f_i(x, y)$ is a reconstructed pixel at location x, y for slice i, $$\gamma = \tan^{-1} \frac{x\cos\beta + y\sin\beta}{R + x\sin\beta - y\cos\beta},$$

$$n = \frac{\beta}{2\pi} \frac{Rr_H}{L(\beta, x, y)},$$

$$L^2(\beta, x, y) = (R\sin\beta + x)^2 + (R\cos\beta - y)^2,$$

$g(\gamma-\gamma', n)$ is a filtering function, and $W(\beta, \gamma', x, y)$ is a weighting function.

30. A device as recited in claim 29, wherein said back projection range circuit sets back projection limits as $\beta_2(x, y) - \beta_1(x,y) = \pi + 2\gamma_m$, where $2\gamma_m$ is a fan angle of an x-ray beam.

31. A device as recited in claim 29, wherein said back projection circuit uses a minimal set of projection data to perform said back projection.

32. A device as recited in claim 29, wherein said back projection circuit uses substantially all of projection data to perform said back projection.

33. A device as recited in claim 26, comprising:
a detector having a plurality of rows;
means for producing projection data; and
means for sorting said projection data using:

$\theta = \beta + \gamma$;

$t = R \sin \gamma$;

and $n' = n - (\gamma/2\pi) r_H$;

where:

$r_H$ is a helical pitch ratio;

R is a distance from an x-ray source to a focal point;

n is an index of a detector row before sorting;

n' is an index of a detector row after sorting;

β is an angle between a y-axis and a central ray of an x-ray beam;

γ is an angle of a ray sum within a projection given by β; and

θ is a view angle after sorting with respect to an x-axis.

34. A device as recited in claim 26, wherein said back-projecting circuit uses:

$$f_i(x, y) = \frac{1}{\pi} \int_{\theta_1(x,y)}^{\theta_2(x,y)} \omega(\theta, x, y) \int_{-\infty}^{\infty} p(\theta, t', n') g(t - t', n') dt' d\theta$$

where: $f_1(x,y)$ is a reconstructed pixel at location x,y for slice i, $t = x\cos\theta + y\sin\theta,$ $$n' = \frac{\theta}{2\pi} \frac{r_H \cos\gamma}{U(\theta, x, y)},$$

$$U(\theta, x, y) = 1 - \frac{x\sin\theta}{R} + \frac{y\cos\theta}{R},$$

$g(t-t', n')$ is a filtering function, and $\omega(\theta, x, y)$ is one of a weight or interpolation function.

35. A method as recited in claim 34, wherein said back projection circuit uses:

$\theta = \beta + \gamma$;

$t = R \sin \gamma$;

and $n' = n - (\gamma/2\pi) r_H$;

where:

$r_H$ is a helical pitch ratio;

R is a distance from an x-ray source to a focal point;

n is an index of a detector row before sorting;

n' is an index of a detector row after sorting;

β is an angle between a y-axis and a central ray of an x-ray beam;

γ is an angle of a ray sum within a projection given by β; and

θ is a view angle after sorting with respect to an x-axis.

36. A device as recited in claim 34, wherein said back projection range circuit sets back projection limits as $\theta_2(x, y) - \theta_1(x,y) = \pi$.

37. A device as recited in claim 34, wherein said back projection circuit uses a minimal set of projection data to perform said back projection.

38. A device as recited in claim 34, wherein said back projection circuit uses substantially all of projection data to perform said back projection.

39. A device as recited in claim 26, comprising:
a detector for detecting projection data having rows of detector elements, where rows in a central portion of said detector have a first axial pitch and other rows in said detector have a second axial pitch wider than said first axial pitch.

40. An image reconstruction device, comprising:
an x-ray source; and
a detector, disposed opposed to said source, having rows of detector elements, each row having an axial pitch which is constant in a row direction, where rows in a central portion of said detector have a first axial pitch, and other rows in said detector have a second axial pitch wider than said first axial pitch.

* * * * *